（12) United States Patent
Marenus et al.

(10) Patent No.: US 9,566,430 B2
(45) Date of Patent: Feb. 14, 2017

(54) MICROCURRENT-GENERATING TOPICAL OR COSMETIC SYSTEMS, AND METHODS OF MAKING AND USING THE SAME

(75) Inventors: Kenneth D. Marenus, Dix Hills, NY (US); George Cioca, East Quoque, NY (US); Peter J. Lentini, West Babylon, NY (US); Geoffrey Hawkins, Yardley, PA (US); Vasile Ionita-Manzatu, Old Bethpage, NY (US); Liliana S. George, Centerport, NY (US); Mirela C. Ionita-Manzatu, Old Bethpage, NY (US); Raffi Balian, Bay Shore, NY (US); Lavinia C. Popescu, Jackson Heights, NY (US)

(73) Assignee: ELC MANAGEMENT LLC, New York, NY (US)

(*) Notice: Subject to any disclaimer, the term of this patent is extended or adjusted under 35 U.S.C. 154(b) by 0 days.

(21) Appl. No.: 12/388,661

(22) Filed: Feb. 19, 2009

(65) Prior Publication Data

US 2009/0270788 A1    Oct. 29, 2009

Related U.S. Application Data

(60) Provisional application No. 61/047,276, filed on Apr. 23, 2008.

(51) Int. Cl.
  *A61N 1/30* (2006.01)
  *A61K 8/02* (2006.01)
  (Continued)

(52) U.S. Cl.
  CPC ............ *A61N 1/303* (2013.01); *A61K 8/0208* (2013.01); *A61K 8/042* (2013.01); *A61N 1/0436* (2013.01);
  (Continued)

(58) Field of Classification Search
  CPC .................. A61K 9/7023; A61K 2800/5424; A61K 2800/5426; A61K 2800/83; A61N 1/0436; A61N 1/044; A61N 1/0468; A61N 1/0492; A61N 1/0496; A61N 1/303; A61N 1/328; A61Q 19/00; A61Q 19/08; C02F 1/005; C02F 1/4618
  (Continued)

(56) References Cited

U.S. PATENT DOCUMENTS 5,246,417 A    9/1993   Haak et al.
5,624,415 A    4/1997   Cormier et al.
(Continued)

FOREIGN PATENT DOCUMENTS

GB    2335142       9/1999
JP    H06-66701    9/1994
(Continued)

OTHER PUBLICATIONS http://www.powerpaper.com/?categoryId=10625; Power Paper; Technology & Innovation; pp. 1-2; Apr. 14, 2009.
(Continued)

*Primary Examiner* — Imani Hayman
*Assistant Examiner* — Larry R Wilson
(74) *Attorney, Agent, or Firm* — Peter Giancana

(57) ABSTRACT

The present invention relates to a topical or cosmetic system that includes a first element capable of acting as an electron donor and a second element capable of acting as an electron acceptor. Such first and second elements are spaced apart by a predetermined distance across a skin surface. The system also includes a third element extending over the predetermined distance across the skin surface, while the third element contains an electrically conductive medium for electrically connecting the first and second elements,
(Continued)

thereby generating an electrical current that flows across the skin surface from the first element through the conductive medium to the second element in the absence of any power source. The present invention also relates to methods of using the above-described system for preventing or treating skin damage.

7 Claims, 6 Drawing Sheets

(51) Int. Cl.
*A61K 8/04* (2006.01)
*A61Q 19/00* (2006.01)
*A61Q 19/08* (2006.01)
*A61N 1/32* (2006.01)
*A61K 9/00* (2006.01)
*A61K 9/70* (2006.01)
*A61N 1/04* (2006.01)

(52) U.S. Cl.
CPC .............. *A61N 1/0492* (2013.01); *A61N 1/328* (2013.01); *A61Q 19/00* (2013.01); *A61Q 19/08* (2013.01); *A61K 9/0009* (2013.01); *A61K 9/0014* (2013.01); *A61K 9/7023* (2013.01); *A61K 2800/5424* (2013.01); *A61K 2800/5426* (2013.01); *A61K 2800/83* (2013.01); *A61N 1/044* (2013.01); *A61N 1/0468* (2013.01)

(58) Field of Classification Search
USPC .......................... 604/20, 289, 290, 500, 501
See application file for complete search history.

(56) References Cited

U.S. PATENT DOCUMENTS

| | | | |
|---|---|---|---|
| 5,772,688 A | 6/1998 | Muroki | |
| 5,846,397 A | 12/1998 | Manzatu et al. | |
| 5,944,685 A | 8/1999 | Muroki | |
| 6,139,855 A * | 10/2000 | Cioca et al. | 424/401 |
| 6,231,874 B1 | 5/2001 | Cioca et al. | |
| 6,289,241 B1 | 9/2001 | Phipps | |
| 6,306,384 B1 | 10/2001 | Lahanas et al. | |
| 6,451,328 B1 | 9/2002 | Ionita-Manzatu et al. | |
| 6,622,037 B2 | 9/2003 | Kasano | |
| 6,905,523 B2 | 6/2005 | Vainshelboim et al. | |
| 6,958,163 B2 | 10/2005 | Ionita-Manzatu et al. | |
| 7,323,198 B2 | 1/2008 | Ionita-Manzatu et al. | |
| 7,476,221 B2 | 1/2009 | Sun et al. | |
| 7,476,222 B2 | 1/2009 | Sun et al. | |
| 7,477,939 B2 | 1/2009 | Sun et al. | |
| 7,477,940 B2 | 1/2009 | Sun et al. | |
| 7,477,941 B2 | 1/2009 | Sun et al. | |
| 7,479,133 B2 | 1/2009 | Sun et al. | |
| 7,480,530 B2 | 1/2009 | Sun et al. | |
| 8,475,689 B2 | 7/2013 | Sun et al. | |
| 2001/0029347 A1 | 10/2001 | Kasano | |
| 2002/0187203 A1 | 12/2002 | Cioca et al. | |
| 2003/0120138 A1 | 6/2003 | Kurnik et al. | |
| 2005/0004550 A1 | 1/2005 | Sun et al. | |
| 2005/0010161 A1 * | 1/2005 | Sun et al. | 604/20 |
| 2005/0192636 A1 * | 9/2005 | Skiba et al. | 607/2 |
| 2006/0275351 A1 * | 12/2006 | Mohammadi et al. | 424/448 |
| 2007/0187327 A1 | 8/2007 | George et al. | |
| 2009/0069740 A1 | 3/2009 | Visco et al. | |
| 2009/0270788 A1 | 10/2009 | Marenus et al. | |

FOREIGN PATENT DOCUMENTS

| | | |
|---|---|---|
| JP | 8173554 | 7/1996 |
| JP | H11-322527 | 11/1999 |
| JP | 2001-502942 | 3/2001 |
| JP | 3748278 | 2/2006 |
| JP | 2007-537767 | 12/2007 |
| WO | WO98/14237 | 4/1998 |
| WO | WO2005/004979 | 1/2005 |
| WO | WO2007/086057 | 8/2007 |

OTHER PUBLICATIONS http://www.powerpaper.com/index.php?categoryId=10735; Power Paper; Mode of Action; pp. 1-2; Apr. 14, 2009.
http://www.powerpaper.com/index.php?categoryId=10834; Power Paper; Printed Electronics; pp. 1-4; Apr. 14, 2009.
http://www.powerpaper.com/index.php?categoryId=19940; Power Paper; Application Guidelines for Hydro-Gel Eye Contour Patches; pp. 1-3; Apr. 14, 2009.
http://www.powerpaper.com/index.php?categoryId=19941; Power Paper; Application Guidelines for NW Eye Contour Patches; pp. 1-3; Apr. 14, 2009.
http://www.powerpaper.com/index.php?categoryId=10740; Power Paper; Anti-Aging treatment; pp. 1-3; Apr. 14, 2009.
Carley, et al.; Electrotherapy for Acceleration of Wound Healing: Low Intensity Direct Current; Arch Phys Med Rehabil; vol. 66; pp. 443-446; 1985.
Chao, et al.; Effects of Applied DC Electric Field on Ligament Fibroblast Migration and Wound Healing; Informa Healthcare; Connective Tissue Research; 48:188-197; 2007.
Alvarez, et al.; The Healing of Superfiscal Skin Wounds is Stimulated by External Electrical Current; The Journal of Investigative Dermatology; vol. 81; No. 2; pp. 144-148; 1983.
Balakatounis, et al.; Low-intensity Electrical Stimulation in Would Healing: Review of the Efficacy of Externaly Applied Currents Resembling the Current of Injury; Open Access Journal of Plastic Surgery; vol. 8; pp. 283-291;2008.
Edelberg Robert, Ph.D.; Rutgers Medical School; The Biophysical Properties of the Skin; Harry Elden (ed.); Chapter 15; Wiley Interscience; pp. 513-550; 1971.
Barker, et al.; The glabrous epidermis of cavies contains a powerful battery; American Journal Physiological; 242 (Regulatory Integrative Comp. Physiol, 11); pp. R358-R365; 1982.
PCT International Search Report; International Application No. PCT/US2009/034456; Completion Date: Oct. 12, 2009; Date of Mailing: Oct. 13, 2009.
PCT Written Opinion of the International Searching Authority, or the Declaration; International Application No. PCT/US2009/034456; Completion Date: Oct. 12, 2009; Mailing Date: Oct. 13, 2009.
Supplementary European Search Report; EP09733894.1; Completion Date: Sep. 19, 2013; Date of Mailing: Oct. 2, 2013.
Supplementary European Search Report; EP10789895.9; Completion Date: Jan. 9, 2014 ; Date of Mailing: Jan. 24, 2014.
PCT International Search Report; International Application No. PCT/US2010/031917; Completion Date: Dec. 22, 2010; Date of Mailing: Dec. 23, 2010.
PCT Written Opinion of the International Searching Authority, or the Declaration; International Application No. PCT/US2010/031917; Completion Date: Dec. 22, 2010; Mailing Date: Dec. 23, 2010.

* cited by examiner

MICROCURRENT-GENERATING TOPICAL OR COSMETIC SYSTEMS, AND METHODS OF MAKING AND USING THE SAME

The present application claims priority from U.S. 61/047,276, filed Apr. 23, 2008.

FIELD OF THE INVENTION

The present invention relates to novel topical or cosmetic systems and skin treatment methods. Specifically, the invention relates to topical or cosmetic systems that, when applied to a skin surface, consistently generate a mild electrical current that flows across the skin surface in a sustainable manner and in absence of any external power source. More specifically, such electrical current is characterized by a current intensity particularly effective for preventing or reducing skin damage and improving skin quality without causing any irritation or inflammation.

BACKGROUND OF THE INVENTION

It has long been recognized that there is a normal transcutaneous electric potential associated with mammalian skin (see, e.g., Robert Edelberg, in, The Biophysical Properties of the Skin, Harry Elden (ed.), Chapter 15, Wiley Interscience, 1971). This potential is to a great extent influenced by the presence of sweat glands and hair, and thus the strength of the potential may differ both spatially and temporally on the skin. However, even in nonglandular areas of the skin, there is a fairly strong, measurable current produced across the epidermis, in essence forming an intrinsic skin battery. Although most measurements have been conducted on non-human mammals, considerable evidence indicates that the same type of battery exists on human skin as well (Barker et al., Am. J. Physiol. 242: R358-R366, 1982). Such batteries have been known to exist in amphibians, where they apparently serve a function in sodium uptake and appendage regeneration. However, their purpose in a nonaquatic vertebrate was not readily apparent. Based on observations of fairly strong voltage gradients at the margins of wounds, Barker et al. and others have suggested that in mammals the skin currents may be important in the process of wound healing.

Further evidence of the importance of electrical currents in the maintenance of healthy skin has been shown in the successful use of electrotherapy in treatment of skin damages. For example, Carley and Wainapel (Arch. Phys. Med. Rehabil. 66: 443-446, 1985) have shown that treatment of indolent ulcers with low intensity direct current significantly increased the healing rate of those treated individuals relative to individuals treated with conventional therapy, with a concomitant reduction in pain and discomfort in those treated with electrotherapy. Similarly, Grace Chao et al. (Connective Tissue Research, 48: 188, 2007) noted the effects of applied DC electric field on the ligament fibroblast migration and wound healing processes, and Alvarez O M et al. (J. Invest. Dermatol., 81(2): 144-148, 1983, August) demonstrated that the healing of superficial skin wounds was stimulated by external electrical current.

Therefore, it appears that the maintenance of an electric current on the skin is associated with the continued well-being of undamaged skin, and that application of an electrical current to damaged skin can be highly beneficial to the healing process of such damaged skin. In addition to the reported treatment of ulcers, there are a number of other skin conditions involving irritation or inflammation which could also potentially benefit from preventive and/or therapeutic application of a low intensity current. However, the means for delivery of electrical current to skin reported in the medical literature typically involve the use of external power source and monitoring devices, which would be prohibitively expensive and complicated for the treatment of less serious skin damages, which are not life-threatening but nonetheless painful and irritating.

Although dermal patches featuring ultra-thin power supplies and electrodes printed or laminated onto elastic and flexible plastic substrates have become commercially available in recent years, such dermal patches are mostly designed for aiding transdermal delivery of active cosmetic or pharmaceutical ingredients into the skin. FIG. 1 illustrates a typical dermal patch used for conventional transdermal delivery of active cosmetic or pharmaceutical ingredients into the skin, which contains a printed, ultra-thin micro battery connected to an anode and a cathode that are in direct contact with the skin surface. The electrical potential differences between the anode and the cathode, as provided by the micro battery, generate an electric current that flows from the anode through the skin to the cathode, which in turn asserts repulsive electromotive forces on charged active cosmetic or pharmaceutical ingredients on the skin surface, i.e., the positively charged anode will repel positively charged active cosmetic or pharmaceutical ingredients into the skin, while the negatively charged cathode will repel negatively charged active cosmetic or pharmaceutical ingredients into the skin.

However, the current intensity achieved by such conventional dermal patch is typically in the milli-ampere (mA) range, which may cause irritation or inflammation of the skin. Further, because the electric current generated by such conventional dermal patch flows through the skin, the current intensity is significantly affected by various factors, such as the pH, moisture content, and resistance of skin, which can vary widely from person to person and even for the same person at different times of the day. In addition, the conventional dermal patches still require presence of power supplies, which significantly increase the complexity and costs of manufacturing and present additional modes of failure.

In contrast with the conventional devices described hereinabove, the present invention provides a simple and novel system for consistently generating a mild electrical current that flows across the skin surface, instead of through the skin, in a sustainable manner without the need for any external power source. Inventors of the present invention have discovered that such mild cross-flow electrical current is surprising and unexpectedly effective for preventing or treating skin damage and improving skin quality, even in absence of any cosmetic or skin care actives.

SUMMARY OF THE INVENTION

The present invention in one aspect relates to a topical or cosmetic system for preventing or treating skin damage, comprising:
  (a) a first element capable of acting as an electron donor;
  (b) a second element capable of acting as an electron acceptor, wherein the first and second element are spaced apart by a predetermined distance across a skin surface; and
  (c) a third element extending over the predetermined distance across the skin surface, wherein the third element comprises an electrically conductive medium for electrically connecting the first and second elements, thereby generating an electrical current that flows across the skin surface through the conductive medium in the absence of any power source.

Another aspect of the present invention relates to a topical or cosmetic device for preventing or treating skin damage, comprising a substrate patch having at least one side with sufficient adhesiveness for application to a skin surface, wherein a first region of the substrate patch comprises at least one component capable of acting as an electron donor, wherein a second region of the substrate patch comprises at least one component capable of acting as an electron acceptor, the first and second regions are spaced apart by a predetermined distance across the skin surface, and wherein the substrate patch comprises an electrically conductive medium for electrically connecting the electron donor component at the first region and the electron acceptor component at the second region, thereby generating an electrical current that flows across the skin surface through the substrate patch in the absence of any power source.

A further aspect of the present invention relates to a unit package comprising:
(a) a first container containing a first topical or cosmetic composition capable of acting as an electron donor;
(b) a second container containing a second topical or cosmetic composition capable of acting as an electron acceptor; and
(c) a third container containing a third topical or cosmetic composition comprising an electrically conductive medium.

A still further aspect of the present invention relates to a unit package comprising:
(a) a first container containing a first topical or cosmetic composition capable of acting as an electron donor;
(b) a second container containing a second topical or cosmetic composition capable of acting as an electron acceptor; and
(c) a substrate patch comprising an electrically conductive medium, wherein said substrate patch has sufficient adhesiveness for application to a skin surface.

Yet another aspect of the present invention relates to a method for preventing or treating skin damages, comprising generating an electric current that flows across a skin surface by using an electron-donating element and an electron-accepting element that are spaced apart from each other and are electrically connected together by an electrically conductive medium extending over such skin surface in the absence of any power source, wherein the electric current has a current intensity ranging from about 1 µA to about 1000 µA.

Other aspects and features of the present invention will become more apparent from the following detailed description with reference to the accompanying drawings.

DETAILED DESCRIPTION OF THE INVENTION, AND PREFERRED EMBODIMENTS THEREOF

It is to be understood that the invention is not limited to the details of construction and arrangement of specific components set forth in the following description, which is directed to preferred embodiments of the present invention and by no means should be construed as limiting the broad scope of the present invention. The present invention is applicable to, and intended to cover, other embodiments not specifically described herein, as long as such embodiments are consistent with the general principles and spirit of the present invention.

The present invention overcomes various deficiencies of prior art devices as described in the Background section, by employing a micro electrical current that flows across the skin surface, instead of through the skin, for preventing or treating skin damage and improving overall appearance of the skin. Further, the present invention provides a simple and innovative system or device for generating such a micro electrical current in a sustainable manner without the need for any external power source.

The principles and operation of the systems and devices of the present invention can be better understood with references to the exemplary embodiments illustrated in the following drawing figures.

Figure 1:
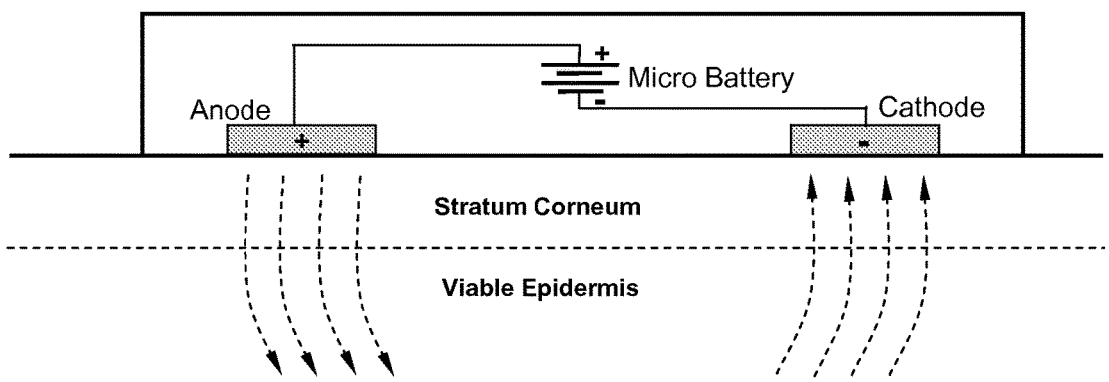
FIG. 1 is a schematic view of a prior art device containing a micro battery connected to an anode and a cathode for facilitating transdermal delivery of active cosmetic or pharmaceutical ingredients into the skin.
Figure 2:
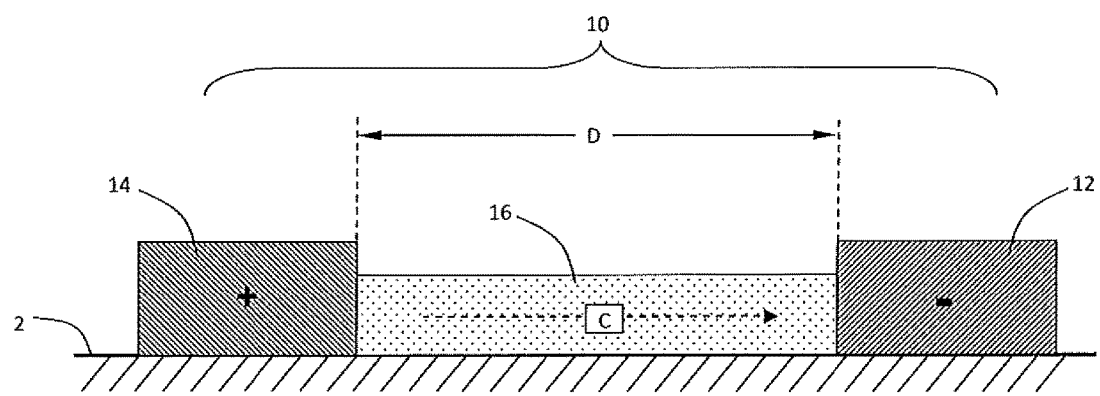
FIG. 2 is a schematic view of a topical or cosmetic system for generating a mild electric current across a skin surface in absence of any power source, according to one embodiment of the present invention.

FIG. 2 shows a schematic view of a topical or cosmetic system 10 as applied to a skin surface 2, according to one embodiment of the present invention. Specifically, the topical or cosmetic system 10 includes a first element 12 and a second element 14 that is spaced apart from element 12 by a predetermined distance "D" across the skin surface 2. The first element 12 has a relatively high standard oxidation potential, in comparison with the second element 14. Therefore, the first element 12 is capable of acting as an electron donor (i.e., a negative electrode or a cathode) and releasing electrons, while the second element 14 is capable of acting as an electron receptor (i.e., a positive electrode or an anode)

and gaining the electrons released by element 12 through an external circuit. The system 10 also includes a third element 16, which extends over the predetermined distance between elements 12 and 14 across the skin surface 2 and which comprises an electrically conductive medium. In this manner, the third element 16 forms an external circuit that electrically connects the first and second elements 12 and 14 together. Correspondingly, an electrical current "C" (as indicated by the arrowhead with a dotted line) is generated in the absence of any power source, which is characterized by a current intensity in the micro-ampere (μA) range and flows between the first and second elements 12 and 14 along a path that extends across the skin surface 2, instead of through the skin. Such a cross-flow microcurrent has demonstrated surprising and unexpected effectiveness in preventing or treating skin damages and improving the overall appearance of the skin. Further, because its flow path extends through the conductive medium of the third element 16 across the skin surface 2, instead of through the skin, the cross-flow microcurrent generated by the topical or cosmetic system of the present invention is significantly less affected by variations in the pH, moisture content, and resistance of the skin, in comparison with the prior art dermal patch devices described in the Background section.

The first and second elements 12 and 14 may comprise any suitable materials or compositions with sufficiently different standard oxidation potentials, and the third element 16 may comprise any suitable electrically conductive medium with sufficient conductivity, so as to generate an electrical current with a current intensity preferably ranging from about 1 μA to about 1000 μA, more preferably from about 5 μA to about 800 μA, and most preferably from about 300 μA to about 700 μA.

In a preferred embodiment of the present invention, the first element 12 comprises a topical or cosmetic composition that comprises one or more electron donor components in a cosmetically or pharmaceutically acceptable carrier, while the second element 14 comprises a topical or cosmetic composition that comprises one or more electron acceptor components in a cosmetically or pharmaceutically acceptable carrier. Examples of electron donor components suitable for incorporation into the topical or cosmetic composition of the present invention include, but are not limited to: (1) I-structured water comprising negatively charged clusters of water molecules; (2) ions or molecules capable of donating electrons, such as certain elemental metals or metal ions with relatively high oxidation potentials, which are capable of releasing electrons; (3) negatively charged molecules, such as certain amino acids (e.g., L-glutamic acid, L-aspartic acid, and the like) and anionic polymers (e.g., polyacrylic acid, polyacrylamide, polyvinylidene pyrrolidone, poly(acrylimidomethylpropane) sulfonate, carageenan, and the like); and (4) combinations of one or more of the above-described components. Examples of electron acceptor components suitable for incorporation into the topical or cosmetic composition of the present invention include, but are not limited to: (1) S-structured water comprising positively charged clusters of water molecules; (2) ions or molecules capable of accepting electrons, such as certain elemental metals or metal ions with relatively low oxidation potentials, which are capable of gaining electrons; (3) positively charged molecules, such as certain amino acids (e.g., L-arginine, L-proline, and the like) or cationic polymers (e.g., polyethylenimine, polydimethyldiallyl ammonium chloride, polymethacrylamidopropyltrimethyl- ammonium chloride, chitosan, polyquaterniums, and the like); and (4) combinations of the one or more of the above-described components.

Structured waters, such as I water and S water, as well as the methods of forming same, have been described in detail by Romanian Patents No. RO 88053, RO88054, RO 107544, RO 107545, and RO 107546; UK Patent Application Publication No. GB2335142; U.S. Pat. Nos. 5,846,397, 6,139,855, 6,231,874, 6,451,328, 6,905,523, 6,958,163, and 7,323,198; and U.S. Patent Application Publications No. 20020187203 A1 and 20070187327 A1, the contents of which are incorporated herein by reference in their entireties for all purposes. Specifically, I and S waters are derived from feed water which has a conductivity of about 250 to about 450 C (μS/cm) and a pH of about 5.0 to about 7.5 through interaction of the dipolar molecular structure of such feed water with an electrical field generated by a particular electromagnetic device, which simultaneously produces the I and S waters. I water comprises negatively charged clusters of water molecule and is characterized by a conductivity of about 500 to about 3500 C (μS/cm) and a pH of about 2.0 to about 4.0. In contrast, S water comprises positively charged clusters of water molecules and is characterized by a conductivity of about 600 to about 2500 C (μS/cm) and a pH of about 10.0 to about 12.0. The known characteristics of structured waters and the devices and processes for producing same are not repeated here in order to avoid obscuring the present invention.

It has been discovered by the inventors that structured waters, such as I water and S water, demonstrate sufficient electron-donating or electron-accepting capacities and therefore can be used in the first and second elements of the topical or cosmetic system as electron donor and acceptor described hereinabove for generating the cross-flow microcurrent over the skin surface. For example, the first element may simply contain a first topical or cosmetic composition formulated with I water, and the second element may simply contain a second topical or cosmetic composition formulated with S water. Alternatively, electron-donating and electron-accepting ions or molecules can be added to the first and second topical or cosmetic compositions, which can in turn bond with the negatively or positively charged clusters of water molecules in I or S water, to further enhance the oxidation potential difference between the first and second elements and thereby increase the current intensity the cross-flow microcurrent to be generated.

In a specific embodiment of the present invention, the topical or cosmetic compositions in the first and second elements contain metal or mineral ions as bound to the negatively or positively charged clusters of water molecules of the I or S water. Any suitable metal or mineral ions with electron-donating or electron-accepting characteristics can be incorporated into the structured waters of the present invention. Examples of suitable metal or mineral ions include, but are not limited to: copper, manganese, selenium, silicon, zinc, iron, aluminum, calcium, potassium, sodium, lithium, magnesium, silver, gold, platinum, and palladium. More specifically, mineral ions contained in water-insoluble minerals or gem stones, such as malachite, azurite, chrysocolla, rhodochrosite, rhodonite, tourmaline, ruby, calcite, hematite, and the like, can be added into the structured waters to form the first and second topical or cosmetic compositions. The concentration of the metal or mineral ions in such compositions may vary, depending on the type of metal or mineral ions used and the desired current intensity of the cross-flow microcurrent to be generated. Typically, the concentration of the metal or mineral ions in the compositions of the present invention may range from about 2 ppm to about 2000 ppm.

In another specific embodiment of the present invention, the topical or cosmetic compositions in the first and second elements contain negatively or positively charged molecules as bound to the negatively or positively charged clusters of water molecules of the I or S water. For example, certain negatively charged amino acids, such as L-glutamic acid and L-aspartic acid, can be added into I water to form the first topical or cosmetic composition in the first element, while certain positively charged amino acids, such as L-arginine and L-proline, can be added into S water to form the second topical or cosmetic composition in the second element. For another example, certain anionic polymers, such as polyacrylic acid, polyacrylamide, polyvinylidene pyrrolidone, poly(acrylimidomethylpropane)sulfonate, carageenan, and the like, can be formulated into the first topical or cosmetic composition of the first element, while certain cationic polymers, such as polyethylenimine, polydimethyldiallyl ammonium chloride, polymethacrylamidopropyltrimethylammonium chloride, chitosan, polyquaterniums, and the like, can be formulated into the second topical or cosmetic composition of the second element.

In a preferred embodiment of the present invention, the first and second elements comprise two different elemental metals, which have sufficiently different standard oxidation potentials, so that one of such elemental metals (i.e., the one with the relatively higher standard oxidation potential) can act as the electron donor and the other (i.e., the one with the relatively lower standard oxidation potential) can act as the electron acceptor. For example, the first element may comprise elemental metals with positive standard oxidation potential, such as those selected from the group consisting of copper, mercury, silver, gold, and the like, and the second element may comprise elemental metals with negative standard oxidation potential, such as those selected from the group consisting of aluminum, zinc, iron, cobalt, nickel, tin, lead, and the like. More preferably, the first and second elements comprise either pure metal strips composed of different elemental metals or fabric strips that are coated with different elemental metals. Most preferably, the first element comprises a copper or silver strip or a fabric strip coated with copper or silver, and the second element comprises an alumina strip or a fabric strip coated with alumina.

The electrically conductive medium contained by the third element 16 as shown in FIG. 2 may comprise any material or materials with sufficiently high electrical conductivity for generating the desired cross-flow microcurrent over the skin surface. Preferably, the electrically conductive medium as employed in the system of the present invention is selected from the group consisting of: (1) electrolyte solutions containing inert electrolytes, such as sodium chloride, potassium chloride, and the like; (2) hydrogels, such as those typically used for forming medical electrodes (e.g., those composed of crosslinked polymers like polyethylene oxide, poly(2-acrylamido-2-methyl-1-propanesulfonic acid) or poly AMPS, and polyvinylpyrrolidone); (3) conductive adhesives, such as glycidyl ether epoxy resin, phenoxy resins, and the like; and (4) combinations thereof.

Hydrogel is a particularly preferred electrically conductive medium for practice of the present invention, which comprises a network of polymer chains that are water-insoluble and dispersed in an aqueous medium, thereby forming a colloidal gel. Hydrogel can be formed of synthetic polymers, such as crosslinked polyethylene oxide, crosslinked poly(2-acrylamido-2-methyl-1-propanesulfonic acid) or poly AMPS, crosslinked polyvinylpyrrolidone, polyvinyl alcohol, sodium polyacrylates, acrylate polymers and copolymers with abundant hydrophilic groups, as well as natural polymers, such as agarose, methylcellulose, hylaronan, and the like. Correspondingly, the third element 16 may consist essentially of hydrogel, which has sufficient adhesiveness and can be readily applied to a skin surface and stay thereon. Element 16 may also comprise hydrogel saturated with an aqueous electrolyte solution. The third element 16 may also simply contain an aqueous solution of an electrolyte such as sodium chloride or potassium chloride, which can be directly applied to a skin surface. Further, the third element 16 may include a non-conductive substrate layer with a conductive adhesive coating. The arrangement and construction of element 16 can be readily modified by a person ordinarily skilled in the art according to specific requirements for the system 10, and the scope of the present invention is thus not limited to any specific arrangement and construction described hereinabove.

The topical or cosmetic system of the present invention is preferably embodied in a patch-like cosmetic article or device with relatively simple structure and fewer components, in comparison with conventional dermal patches typically used for transdermal delivery of active cosmetic or pharmaceutical ingredients into the skin. Such a patch-like cosmetic device can be easily manufactured at relatively low costs and readily applied to a skin surface for treatment thereof with few pre-treatment or preparation steps. For example, the present invention may provide a topical or cosmetic patch that includes a substrate patch with at least one side having sufficient adhesiveness for application to a skin surface. A first region of this substrate patch includes at least one component capable of acting as an electron donor, and a second region of this patch includes at least one component capable of acting as an electron acceptor. The first and second regions are spaced apart from each other by a predetermined distance across the skin surface to which the substrate patch is applied. The substrate patch further includes an electrically conductive medium, which electrically connects the electron donor component at the first region with the electron acceptor component at the second region, thereby generating an electric current that flows through the substrate patch across the skin surface in the absence of any power source. The composition and construction of the substrate may be similar to the element 16 in FIG. 2, and the compositions and constructions of the first and second regions may be similar to the elements 12 and 14 in FIG. 2, as described hereinabove.

Figure 3A:
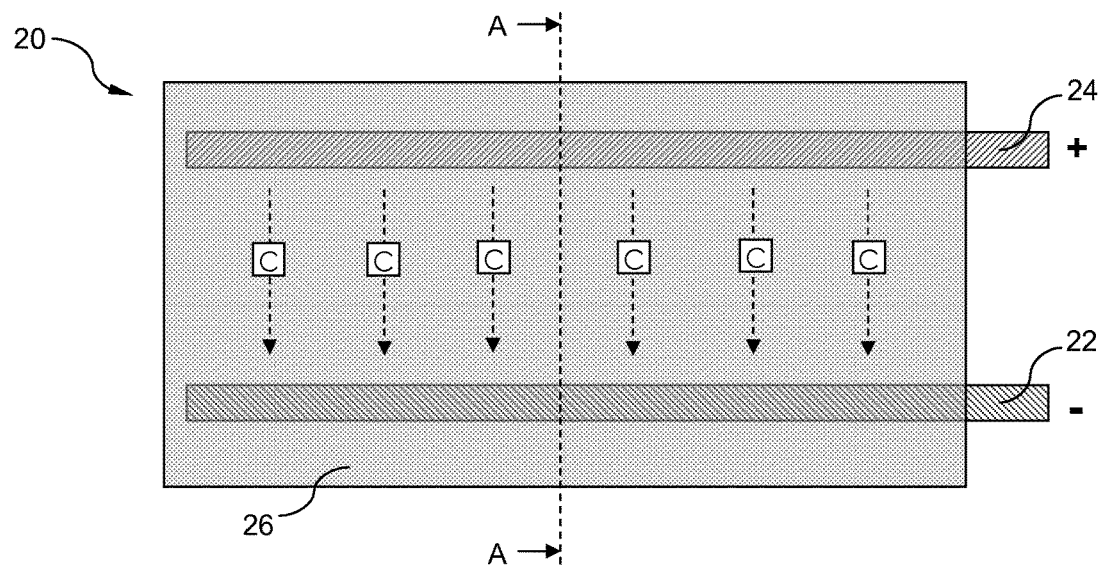
FIG. 3A is a top view of a topical or cosmetic device that contains a substrate patch consisting essentially of hydrogel, a first metal strip capable of acting as an electron donor, and a second metal strip capable of acting as an electron acceptor, according to one embodiment of the present invention.
Figure 3B:
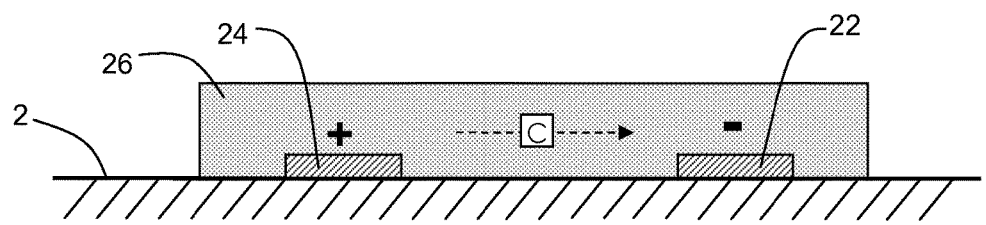
FIG. 3B is a cross-sectional view of the topical or cosmetic device of FIG. 3A along the A-A line, as applied to a skin surface.

FIGS. 3A and 3B show the top and cross-section views of a patch-like topical or cosmetic device 20, according to a specific embodiment of the present invention. Specifically, the device 20 includes a substrate patch 26 preferably formed of hydrogel with sufficient adhesiveness for direct application to a skin surface 2. Optionally, the hydrogel patch 26 may be saturated with or otherwise contain an aqueous electrolyte solution, which further increases the electrical conductivity of the hydrogel patch 26. Two different metal strips or two fabric strips coated with different metals, 22 and 24, are provided on one side of the hydrogel patch 26 in a parallel and spaced-apart relation to each other. The first metal strip or metal-coated fabric strip 22 contains a first elemental metal of a relatively high standard oxidation potential, and the second metal strip or metal-coated fabric strip 24 contains a second elemental metal of a relatively low standard oxidation potential. For example, the first strip 22 may contain one or more elemental metals selected from copper, mercury, silver, gold, and the like, while the second strip 24 may contain one or more elemental metals selected from aluminum, zinc, iron, cobalt, nickel, tin, lead, and the like. In a particularly preferred embodiment of the present invention, the first strip 22 is a copper or silver strip or a copper- or silver-coated fabric strip, and the second strip 24 is an aluminum strip or an aluminum-coated fabric strip. The oxidation potential difference between the first and second strips 22 and 24 generates microcurrents "C" that flow through the hydrogel patch 26 across the skin surface 2 (as indicated by the arrowheads with dotted lines).

Figure 4:
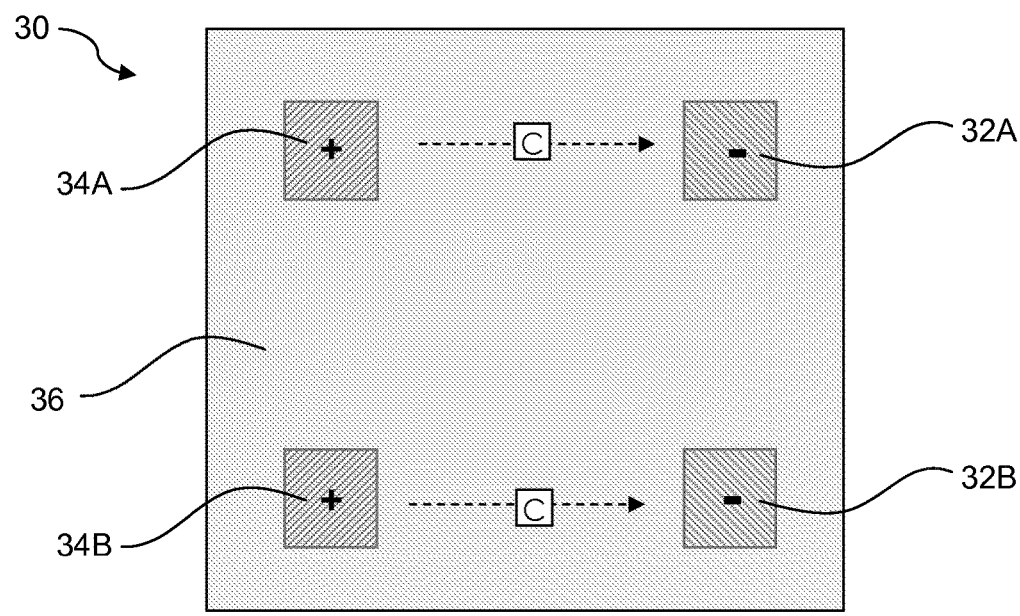
FIG. 4 is a top view of a topical or cosmetic device that contains a substrate patch consisting essentially of hydrogel, two metal squares capable of acting as electron donors, and two metal squares capable of acting as electron acceptors, according to one embodiment of the present invention.

FIG. 4 shows the top view of another patch-like topical or cosmetic device 30, according to another embodiment of the present invention. Specifically, the device 30 includes a substrate hydrogel patch 36, which is optionally saturated with or otherwise contains an aqueous electrolyte solution. Four metal squares or metal-coated fabric squares, 32A, 32B, 34A, and 34B, are provided on one side of the hydrogel patch 36 in a spaced-apart relation to one another. The metal squares or metal-coated fabric squares 32A and 34A contain a first elemental metal of a relatively high standard oxidation potential (e.g., copper, mercury, silver, gold, and the like), and the metal squares or metal-coated fabric squares 32B and 34B contain a second elemental metal of a relatively low standard oxidation potential (e.g., aluminum, zinc, iron, cobalt, nickel, tin, lead, and the like). In a particularly preferred embodiment of the present invention, the metal squares or metal-coated fabric squares 32A and 34A contain copper or silver, and the metal squares or metal-coated fabric squares 32B and 34B contain aluminum. The oxidation potential difference between 32A and 34A as well as that between 32B and 34B produce cross-flow microcurrents "C" that flow through the hydrogel patch 36 across the corresponding skin surface to which the patch 36 is applied (as indicated by the arrowheads with dotted lines).

Figure 5:
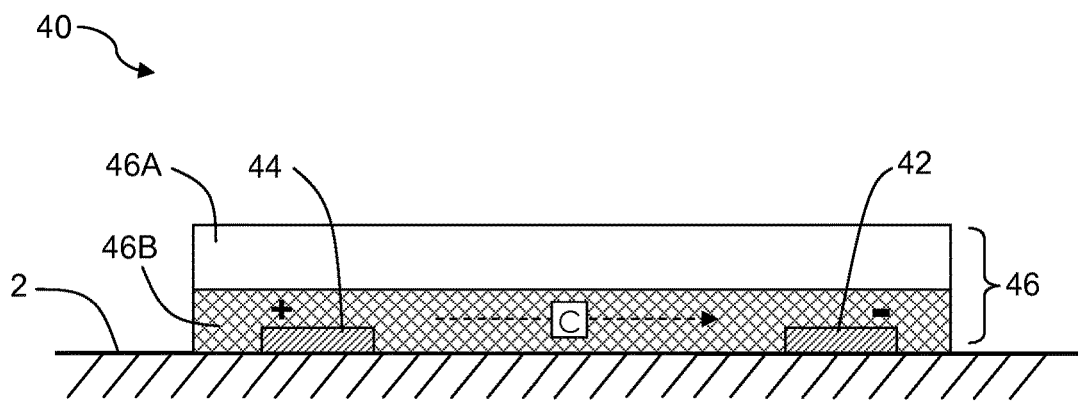
FIG. 5 is a cross-sectional view of a topical or cosmetic device that contains a non-conductive base substrate layer with a conductive adhesive layer coated thereon, while the conductive adhesive layer is in direct contact with a first metal strip capable of acting as an electron donor and a second metal strip capable of acting as an electron acceptor, according to one embodiment of the present invention.

FIG. 5 shows the cross-sectional view of yet another patch-like topical or cosmetic device 40, according to yet another embodiment of the present invention. Specifically, the device 40 includes a dual-layer substrate patch 46 as applied to a skin surface 2, which includes a non-conductive base layer 46A with a conductive adhesive layer 46B coated thereon. The non-conductive base layer 46A may be formed by any non-conductive material with suitable flexibility for application to the skin surface 2 as well as sufficient tensile strength for supporting the conductive adhesive layer 46B. Examples of suitable non-conductive materials that can be used for forming the layer 46A include, but are not limited to: fabrics, papers, polymers, and the like. Two different metal strips or metal-coated fabric strips, 42 and 44, are provided on one side of the substrate patch 46, i.e., the same side as the conductive adhesive layer 46B, in a parallel and spaced-apart relation to each other. The oxidation potential difference between the first and second strips 42 and 44 generates a microcurrent "C" that flows through the conductive adhesive layer 46B of the substrate patch 46 across the skin surface 2 (as indicated by the arrowhead with a dotted line).

Figure 6:
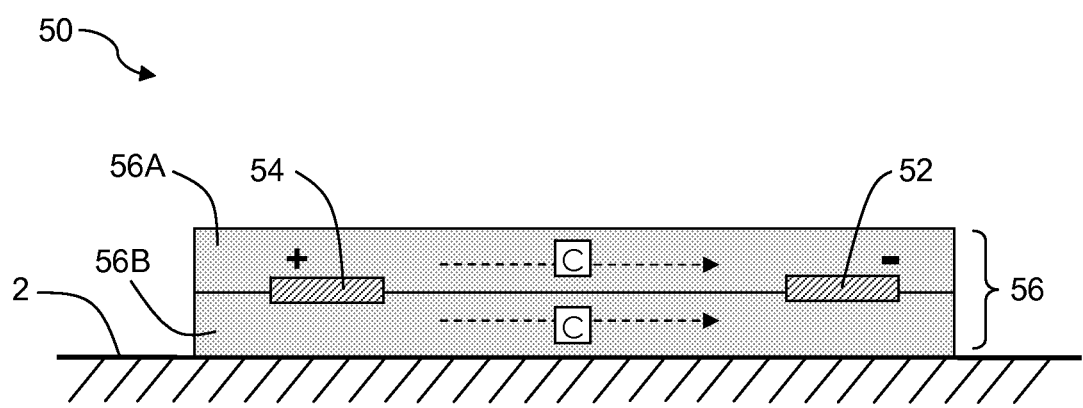
FIG. 6 is a cross-sectional view of a topical or cosmetic device that contains a first metal strip capable of acting as an electron donor and a second metal strip capable of acting as an electron acceptor, while the first and second metal strips are sandwiched between two hydrogel patches, according to one embodiment of the present invention.

FIG. 6 shows the cross-sectional view of a further patch-like topical or cosmetic device 50, according to a further embodiment of the present invention. Specifically, the device 50 includes a substrate patch 56 formed by two hydrogel patches 56A and 56B that are placed back-to-back against each other. The inherent adhesiveness of the hydrogel patches 56A and 56B provides sufficient bonding between such patches as well as sufficient adhesion to the skin surface 2, without the need for any adhesives. Sandwiched between the two hydrogel patches 56A and 56B are two metal strips or metal-coated fabric strips, 52 and 54, which contain different elemental metals of different standard oxidation potentials and are placed in a parallel and spaced-apart relation to each other. The oxidation potential difference between the first and second strips 52 and 54 generates microcurrents "C" that flow through both hydrogel patches 56A and 56B across the skin surface 2 (as indicated by the arrowheads with dotted lines). The sandwich-like arrangement and construction, as described hereinabove, provides better contact between the hydrogel patches 56A and 56B and the strips 52 and 54, as well as a current flow path of higher conductivity. Correspondingly, the current intensity of the microcurrent so generated is further increased and stabilized.

Note that the substrate patch of the present invention may comprise additional layers of conductive and non-conductive materials, as long as the two metal strips or metal-coated fabric strips are in direct electric contact with the same conductive layer, which is to be applied directly onto a skin surface for generation of the cross-flow micro-electric current described hereinabove. Such conductive layer may be covered by a removable non-conductive protective layer for storage purposes, and prior to application to the skin surface, such protective layer is removed so as to allow the conductive layer to directly contact the skin surface.

In order to provide a microcurrent-generating cosmetic patch with extended shelf life, it may be desirable to use a material with a variable electrical conductivity in the substrate patch. Specifically, the material is initially provided in a non-conductive or a less conductive phase, so that little or no electrical current is generated in the substrate patch and the substrate patch can be stored for an extended period of time prior to use without losing the electrical capacitance between the metal strips. At the time of actual use, the material can be converted to a conductive or a more conductive phase via one or more simple treatment steps, so that an electrical current of desired intensity can be generated in the substrate patch for skin treatment. For example, the substrate patch may be initially formed of dried hydrogel, which has little or no electrical conductivity, and at the time of use, the user may wet the dried hydrogel patch with simply water or an aqueous wetting solution that contains additional electrolytes, to form a conductive hydrogel patch that is capable of generating a microcurrent across the skin surface.

In an alternatively embodiment of the present invention, the microcurrent-generating system may be embodied in a unit package that includes different topical or cosmetic composition stored in separate containers prior to use. Since these compositions are stored in separate containers with no interactions therebetween prior to use, the unit package as a whole has a relatively long shelf life. For example, such a unit package includes a first topical or cosmetic composition containing one or more electron donor components, a second topical or cosmetic composition containing one or more electron acceptor components, and a third topical or cosmetic composition containing a electrically conductive medium. These three compositions can be applied sequentially or simultaneously onto a skin surface to form a microcurrent-generating system in situ, i.e., the first composition being applied to a first region on the skin surface, the second composition being applied to a second, spaced-apart region on the skin surface, and the third composition being applied to a region between the first and second region and thereby electrically connecting the first and second region. The unit package may further include a substrate patch with sufficient adhesiveness for direct skin application, and the three compositions can be first applied to respective regions on the substrate patch, which is in turn applied to a skin surface for treatment thereof. For another example, the unit package may include a first topical or cosmetic composition containing one or more electron donor components, a second topical or cosmetic composition containing one or more electron acceptor components, and a substrate patch comprising an electrically conductive medium and having sufficient adhesiveness for direct application to the skin.

The topical or cosmetic compositions as described hereinabove are preferably formulated with pharmaceutically or cosmetically acceptable carriers. The term "pharmaceutically or cosmetically acceptable carrier" refers to a carrier, for either pharmaceutical or cosmetic use, which carrier delivers the active components to the intended target and which will not cause harm to humans or other recipient organisms. As used herein, "pharmaceutical" or "cosmetic" will be understood to encompass pharmaceuticals or cosmetics for both humans and animals. The carrier can be provided in any form convenient for topical application to the skin. Such forms include, but are not limited to gels, creams, dispersions, emulsions (water-in-oil or oil-in-water), suspensions, lotions, foams, mousses and the like.

Because of the skin enhancing effects of the topical or cosmetic compositions of the present invention, they may also have incorporated active skin care agents which are used for skin treatment, or which are routinely applied topically. Examples of such active skin care agents which may form part of the above-described compositions include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active skin care agents include retinoids, topical cardiovascular agents, clotrimazole, ketoconazole, miconazole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21 acetate, hydrocortisone 17-valerate, hydrocortisone 17-butyrate, betamethasone valerate, betamethasone diprorionate, triamcinolone acetonide, fluocinonide, clobetasol, proprionate, benzoyl peroxide, crotamiton, propranolol, promethazine, vitamin A palmitate, vitamin E acetate, DHEA and derivatives thereof, alpha- or beta-hydroxy acids, and mixtures thereof. The amount of active skin care agent to be used in any given composition is readily determined in accordance with its usual dosage. In adding of such further components to the microcurrent-generating system of the present invention, however, consideration should be given to the standard oxidation potentials of the additional components, so that the additional components do not interfere with the intended interactions between the respective elements of the system.

The topical or cosmetic compositions as described hereinabove can be readily prepared by routine mixing methods known to those skilled in the formulation arts. The electron donor/acceptor component, the electrically conductive medium, and the optional active skin care agent can be simply mixed into the chosen carrier and packaged appropriately.

The compositions may further comprise other components which may be chosen depending on the carrier and/or the intended use of the compositions. Additional components include, but are not limited to: water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The microcurrent-generating system of the present invention can be used in a number of different therapeutic or preventive applications. In general terms, since the presence of an electric potential at the skin surface is shown to be characteristic of normal, healthy skin, application of the microcurrent-generating system of the present invention can be employed as a regularly applied preventive of skin damage, e.g. redness and irritation commonly associated with dry skin or exposure to sun, heat and/or cold, and to promote and maintain overall skin health. It can also serve as a spot treatment to reduce the effects of inflammation or irritation on an already damaged skin surface, wherein the treatment can be applied and repeated, as needed. In this regard, the electron donor/acceptor component or the electrically conductive medium may be directly mixed with other skin care actives for use in treatment of skin conditions, as described hereinabove. However, the system of the present invention can also be used alone, i.e., without any skin care additives, for reduction of fine lines, wrinkles, acute or chronic skin damages caused by sun exposure or environmental assaults and also for reduction of irritation and inflammation associated with dry skin, severe dry skin, dandruff, acne, keratoses, psoriasis, eczema, skin flakiness, pruritus, lentigines, melasmas, warts, blemished skin, hyperpigmented skin, hyperkeratotic skin, or inflammatory dermatoses, which conditions may or may not also be treated with a skin active agent. In addition, the microcurrent-generating system or device of the present invention can be used as an adjunct to the wound healing process. As shown above, healing skin is known to be associated with a measurable, increased current. The system and device of the present invention can be used to enhance the naturally occurring process, either by direct combination with wound-healing active agents, or alone in a separate application.

It will be understood by those skilled in the art that the phrase "treatment or prevention of skin damage" as used in the present specification and claims encompasses each of the enumerated specific applications, as well as any not specifically enumerated expressly herein. In particular, it will be understood that "prevention of skin damage" is meant to include routine maintenance of skin health without reference to prevention of a specific skin condition, as well as referring to prevention of specific conditions or problems.

The invention is further illustrated in the following non-limiting examples.

EXAMPLES

Example 1

Cosmetic Patch with Al—Cu Electrodes

A cosmetic patch was formed by placing two identical hydrogel patches (about 2.5 inches in length and 1.5 inches in width) back-to-back. Sandwiched between the two hydrogel patches were two narrow metal-containing strips, one of which was an aluminum foil strip about 6 cm in length and 6 mm in width, and the other of which was a fabric strip about 6 cm in length and 6 mm in width and electro-plated with copper. The two metal-containing strips were spaced apart from each other and positioned in a parallel relationship with a distance of about 1 inch therebetween. Optionally, an electrolyte gel was applied to a top surface of one of the hydrogel patches so as to increase the intensity of the electric current that flowed between the two metal-containing strips through the hydrogel patches. Specifically, the electrolyte gel contained about 91 wt % of deionized water of, about 3 wt % of sodium chloride, about 1 wt % of phenoxyethanol, and about 5 wt % of Sepiplus™ 400 thickener or emulsifier. Sepiplus™ 400 is a new generation of hydro-swelling-droplet thickener or emulsifier that contains about 60 wt % of polyacrylates 13, about 30 wt % of polyisobutene, 5 wt % of polysorbate 20, and 5 wt % of water, and it is commercially available from Seppic, Inc. at Fairfield, N.J.

In order to measure the current intensity of the microcurrent generated by the cosmetic patch, the metal-containing strips were connected with respective electrodes of a sensitive DIGITAL MULTIMETER, Model No. GDM-8034 from Instek Corp. U.S.A., which was designed for measuring various electrical parameters and could measure intensity of direct electrical currents in the microamphere (μA) range, through a 10 ohms resistor. The cosmetic patch was applied to a skin surface, and the current intensity generated by the patch was measured over time. When no electrolyte gel was applied to the top surface of the cosmetic patch, a current intensity peak of about 165 μA was observed within 5 minutes after the measurement commenced. When the above-described electrolyte gel was applied to the top surface of the cosmetic patch, a current intensity peak of about 312 μA was observed within 5 minutes after the measurement commenced.

Example 2

Cosmetic Patch with Al—Ag Electrodes

A cosmetic patch was formed by placing two identical hydrogel patches (about 2.5 inches in length and 1.5 inches in width) back-to-back. Sandwiched between the two hydrogel patches were two metal-containing strips, one of which was an aluminum foil strip about 6 cm in length and 6 mm in width, and the other of which was a fabric strip about 6 cm in length and 6 mm in width and electro-plated with silver. The two metal-containing strips were spaced apart from each other and positioned in a parallel relationship with a distance of about 1 inch therebetween.

In order to measure the current intensity of the microcurrent generated by the cosmetic patch, the metal-containing strips were connected with respective electrodes of the above-described DIGITAL MULTIMETER through a 10 ohms resistor. The cosmetic patch was applied to a skin surface, and the current intensity generated by the patch was measured over time. When no electrolyte gel was applied to the top surface of the cosmetic patch, a current intensity peak of about 694 μA was observed within 5 minutes after the measurement commenced. When the electrolyte gel as described hereinabove in Example 1 was applied to the top surface of the cosmetic patch, a current intensity peak of about 1704 μA was observed within 5 minutes after the measurement commenced.

Example 3

Cosmetic Patch with Cosmetic Compositions as Electrodes

First and second cosmetic compositions containing the following ingredients were formulated by mixing the various phases together in sequence to form homogeneous mixtures.

TABLE 1

First Cosmetic Composition (−)

| Phase | Ingredients | Amount (wt %) |
|---|---|---|
| 1 | I-Malachite Water (I Water bound with Cu ions) | 46.86 |
|   | Disodium EDTA | 0.10 |
|   | Arginine | 0.04 |
| 2 | *Aloe barbadensis* leaf juice | 45.00 |
|   | Aminopropyl ascorbyl phosphate | 0.10 |
|   | Water/sweet almond seed extract | 0.20 |
| 3 | Sodium acrylate/sodium acryloydimethyl taurate copolymer// hydrogenated polydecene//laureth-8 | 2.50 |
| 4 | Hydrogenated polydecene | 3.50 |
| 5 | Caprylyl glycol/phenoxyethanol/ hexylene glycol | 0.50 |
| 6 | Ethylhexylglycerin | 0.20 |

TABLE 2

Second Cosmetic Composition (+)

| Phase | Ingredients | Amount (wt %) |
|---|---|---|
| 1 | S Water | 70.15 |
|   | Glycerin | 6.00 |
|   | Caprylyl glycol | 0.80 |
|   | Sodium stearoyl glutamate | 1.35 |
|   | Isostearamidopropyl dimethylamine | 0.60 |
|   | Algae extract | 0.40 |
|   | Porphyridium polysaccharide hydroxypropyltrimonium chloride | 0.40 |
|   | Methoxy PEG/PPG-7/3 aminopropyl dimethicone | 0.20 |
|   | Caprylyl glycol/phenoxyethanol/ hexylene glycol | 0.70 |
|   | Potassium sorbate | 0.10 |
| 2 | Jojoba seed oil | 10.00 |
|   | Cetyl alcohol | 0.50 |
|   | Hydrogenated lecithin | 0.80 |
| 3 | Dimethicone | 6.00 |
| 4 | Polyacrylate 13/polyisobutene/ polysorbate 20/water | 2.00 |

The first and second cosmetic compositions were applied at about 1 gram per square inch to two separate 5.5 inch×1 inch strips that were spaced apart at a distance of about 1 inch on a skin surface. A hydrogel patch about 15 cm in length and 7.5 cm in width was placed over the skin surface to electrically connect these two spots. One electrode of the above-described DIGITAL MULTIMETER was connected to one spot through a metallic conductor having an electrical resistance of about 0.01-2 ohms, and the other electrode of the DIGITAL MULTIMETER was connected to the other spot through an identical metallic conductor. The intensity of the microcurrent generated by the first and second cosmetic compositions and flowing through the hydrogel patch was measured over time. A current intensity peak of about 181 µA was observed within 5 minutes after the measurement commenced.

Example 4

The first and second cosmetic compositions as described hereinabove in Example 3 were applied at about 0.5 gram per square inch to two separate 5.5 inch×1 inch strips that were spaced apart at a distance of about 1 inch on a skin surface. A hydrogel patch about 15 cm in length and 7.5 cm in width was placed over the skin surface to electrically connect these two spots. One electrode of the above-described DIGITAL MULTIMETER was connected to one spot through a metallic conductor having an electrical resistance of about 0.01-2 ohms, and the other electrode of the DIGITAL MULTIMETER was connected to the other spot through an identical metallic conductor. The intensity of the microcurrent generated by the first and second cosmetic compositions and flowing through the hydrogel patch was measured over time.

Subsequently, the same first and second compositions were applied at about 0.25 gram per square inch to two separate 5.5 inch×1 inch strips spots that were spaced apart at a distance of about 1 inch on a skin surface. A hydrogel patch about 15 cm in length and 7.5 cm in width was placed over the skin surface to electrically connect these two spots. One electrode of the above-described DIGITAL MULTIMETER was connected to one spot through a metallic conductor having an electrical resistance of about 0.01-2 ohms, and the other electrode of the DIGITAL MULTIMETER was connected to the other spot through an identical metallic conductor. The intensity of the microcurrent generated by the first and second cosmetic compositions and flowing through the hydrogel patch was measured over time.

Figure 7:
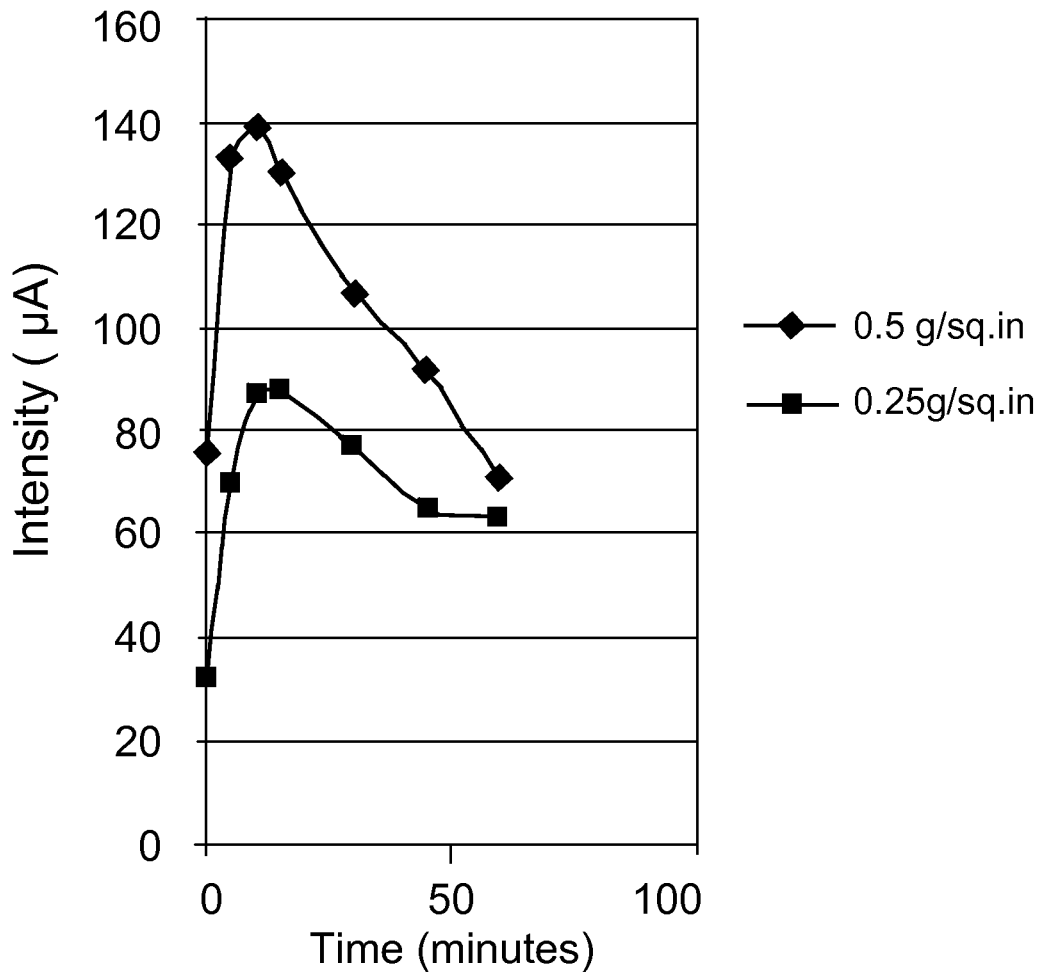
FIG. 7 shows time-dependent current intensity curves of microcurrents generated by two different topical or cosmetic compositions of the present invention applied over a skin surface at different concentrations.

The current intensity curves of the microcurrents generated by the first measurement (at 0.5 g/in$^2$) and the second measurement (at 0.25 g/in$^2$) were plotted as a function of time, as shown in FIG. 7.

Example 5

Cosmetic Patch with I and S Structured Waters as Electrodes

First and second cosmetic compositions containing respectively 100 wt % I water and 100 wt % S water were applied at about 1 gram per square inch to two 6 cm$^2$ spots that were spaced apart at a distance of about 1 inch on a skin surface. A third cosmetic composition containing 1 wt % sodium chloride (NaCl) in distilled water was applied over the skin surface to electrically connect these two spots. One electrode of the above-described DIGITAL MULTIMETER was connected to one spot through a metallic conductor having an electrical resistance of about 0.01-2 ohms, and the other electrode of the DIGITAL MULTIMETER was connected to the other spot through an identical metallic conductor. The intensity of the microcurrent generated by the first and second cosmetic compositions and flowing through the hydrogel patch was measured over time. A current intensity peak of about 13.4 µA was observed within 2 minutes after the measurement commenced.

Example 6

Comparative Studies

The wrinkle-reduction effect of the inventive cosmetic patch as described hereinabove in Example 3 was tested and compared with several control set-ups.

Specifically, the first and second cosmetic compositions were applied at about 1 gram per square inch to two separate 5.5 inch×1 inch strips that were spaced apart at a distance of about 1 inch on the forehead of a human subject. A hydrogel patch about 15 cm in length and 7.5 cm in width was placed over the forehead of the human subject to electrically connect these two spots. The hydrogel patch was removed from the forehead of the human subject after about two hours.

The first control set-up, which was identified hereinafter as "Creams Mixed," was conducted by homogenously mixing the first and second cosmetic compositions, applying the mixture at about 1 gram per square inch to an area of about 15 cm in length and 7.5 cm in width on the forehead of a human subject, and allowing the mixture to stay thereon for about two hours.

The second control set-up, which was identified hereinafter as "Patch Only," was conducted by placing a hydrogel patch of about 15 cm in length and 7.5 cm in width over the forehead of a human subject. The hydrogen patch was removed from the forehead of the human subject after about two hours.

The third control set-up, which was identified hereinafter as "Patch+Creams Mixed," was conducted by homogenously mixing the first and second cosmetic compositions, applying the mixture at about 1 gram per square inch to an area of about 15 cm in length and 7.5 cm in width on the forehead of a human subject, and placing a hydrogel patch about 15 cm in length and 7.5 cm in width was placed over the forehead of the human subject. The hydrogel patch was removed from the forehead of the human subject after about two hours.

The fourth control set-up, which was identified hereinafter as "Power Paper," was conducted by applying the microelectronic patch manufactured by Power Paper Ltd. in Kibbutz Einat, Israel over the forehead of a human subject. The micro-electronic patch was removed from the forehead of the human subject after about two hours.

The photographic images of the forehead of the human subject were taken both before and after each treatment. Each treatment was repeated on three different human subjects, one male and two females, and the corresponding before- and after-photographs were evaluated by ten individuals that were blinded to key so as to determine the difference in skin wrinkleness between the before- and after-photographs. Each evaluation was recorded as a score between 1 and 10, with 1 being the smallest difference and 10 being the largest difference. Following is a table that summarizes the comparative test results:

TABLE 3

| Treatment | Average Score | Standard Deviation |
| --- | --- | --- |
| Inventive Cosmetic Patch | 9.75 | 0.58 |
| Control 1: Creams Mixed | 7.7 | 2.0 |

TABLE 3-continued

| Treatment | Average Score | Standard Deviation |
|---|---|---|
| Control 2: Patch Only | 6.4 | 2.8 |
| Control 3: Patch + Creams Mixed | 5.9 | 2.0 |
| Control 4: Power Paper | 5.9 | 2.0 |

The above-described comparative tests demonstrated the exceptional wrinkle reduction effect of the inventive cosmetic patch, especially in comparison with the controls. Note that in the control set-ups including homogeneously mixed first and second cosmetic compositions, little or no stable electrical current flowed across the skin surface, because the two compositions cancelled each other out in the homogeneous mixture, due to Coulombian attraction, and the resulting electrical current, if any, was thus extremely transient.

While the invention has been described herein with reference to specific aspects, features, and embodiments, it will be recognized that the invention is not thus limited, but rather extends to and encompasses other variations, modifications and alternative embodiments. Accordingly, the invention is intended to be broadly interpreted and construed to encompass all such other variations, modifications, and alternative embodiments, as being within the scope and spirit of the invention as hereinafter claimed.

What we claim is:

1. A topical or cosmetic system for preventing or treating skin damage, comprising:
    (a) a first topical composition comprising I-structured water comprising negatively charged clusters of water molecules, the first topical composition having no S-structured water;
    (b) a second topical composition comprising S-structured water comprising positively charged clusters of water molecules, the second topical composition having no I-structured water; wherein the first and second topical compositions are capable of being spaced apart by a predetermined distance across a skin surface; and
    (c) an electrically conductive medium capable of contacting the skin and extending over the predetermined distance across the skin surface, for electrically connecting the first and second topical compositions,
    thereby generating an electrical current that flows across the skin surface through the conductive medium in the absence of any power source.

2. The system of claim 1, where the electrically conductive medium has a sufficiently high conductivity so that the electrical current so generated has a current intensity ranging from about 1 µA to about 1000 µA.

3. The system of claim 1, wherein the negatively charged clusters of water molecules are bound with ions or molecules that are capable of donating electrons.

4. The system of claim 1, wherein the positively charged clusters of water molecules are bound with ions or molecules that are capable of accepting electrons.

5. The system of claim 1, wherein the negatively charged clusters of water molecules are bound with an anionic polymer, and wherein the positively charged clusters of water molecules bound with a cationic polymer.

6. The system of claim 1, wherein the electrically conductive medium is selected from the group consisting of: (1) electrolyte solutions; (2) hydrogels; (3) conductive adhesives; and (4) combinations thereof.

7. The system of claim 6, wherein the electrically conductive medium comprises a hydrogel.

* * * * *